(12) United States Patent
Gesenberg et al.

(10) Patent No.: US 6,737,428 B2
(45) Date of Patent: May 18, 2004

(54) BIS HYDROCHLORIDE MONOHYDRATE SALT OF RSV FUSION INHIBITOR

(75) Inventors: Christoph Gesenberg, Cheshire, CT (US); David Paul Provencal, Cromwell, CT (US); Srinivasan Venkatesh, Cheshire, CT (US); Hua Wang, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/310,274

(22) Filed: Dec. 5, 2002

(65) Prior Publication Data

US 2003/0114481 A1 Jun. 19, 2003

Related U.S. Application Data

(60) Provisional application No. 60/338,988, filed on Dec. 10, 2001.

(51) Int. Cl.$^7$ .............................................. A61K 31/44
(52) U.S. Cl. ...................................... 514/303; 546/118
(58) Field of Search ........................... 514/303; 546/118

(56) References Cited

U.S. PATENT DOCUMENTS

| | | |
|---|---|---|
| 4,324,794 A | 4/1982 | Tidwell et al. |
| 5,256,666 A | 10/1993 | Mueller et al. |
| 6,489,338 B2 | 12/2002 | Yu et al. |
| 2002/0016309 A1 | 2/2002 | Yu et al. |

Primary Examiner—Amelia A. Owens
(74) Attorney, Agent, or Firm—James Epperson; Samuel J. DuBoff

(57) ABSTRACT

The novel crystalline bis hydrochloride monohydrate salt having the formula

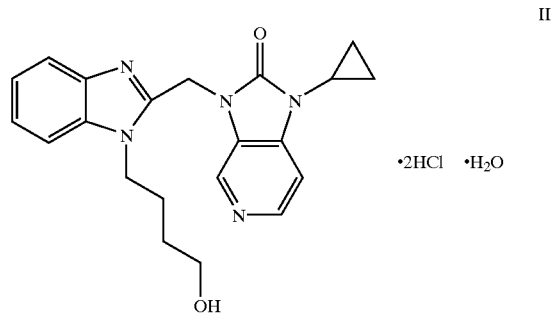

and pharmaceutical dosage forms thereof is provided having use in the treatment of respiratory syncytial viral infection.

2 Claims, 5 Drawing Sheets

BIS HYDROCHLORIDE MONOHYDRATE SALT OF RSV FUSION INHIBITOR

CROSS-REFERENCE TO RELATED APPLICATION

This is a non-provisional application which claims the benefit of U.S. Provisional Application No. 60/338,988 filed Dec. 10, 2001.

FIELD OF THE INVENTION

The present invention provides the novel crystalline bis hydrochloride monohydrate salt of the imidazopyridine RSV (i.e., respiratory syncytial virus) Fusion Inhibitor of the formula

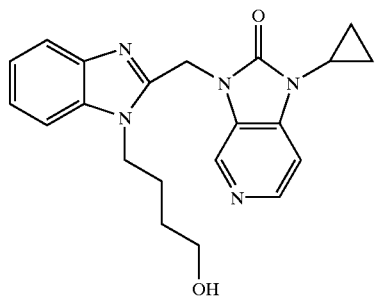

I which exhibits superior physical stability to other salts, and significantly improved aqueous solubility/dissolution behavior and bulk characteristics compared to the free base. The bis hydrochloride monohydrate salt is thus useful for pharmaceutical dosage forms of the above indicated RSV Fusion Inhibitor, particularly for oral dosage forms.

BACKGROUND ART

Commonly-owned U.S. patent application Ser. No. 09/840,279 filed Apr. 3, 2001 discloses a series of imidazopyridine and imidazopyrimidine antiviral agents reported to have a high degree of inhibitory activity against the RSV virus. One of the agents included within the scope is the compound having the structural formula

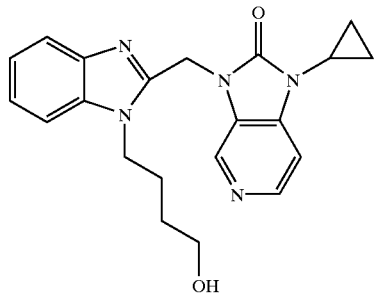

I

This application discloses the free base form of imidazopyridine derivatives such as compound I and also various pharmaceutically acceptable acid addition salts. While several organic and inorganic salts are mentioned as possible salt-forming agents, including hydrochloric acid, there is no mention of the particular bis hydrochloride monohydrate salt which is the subject of the present application.

SUMMARY OF THE INVENTION

The present invention provides the bis hydrochloride monohydrate salt of compound I above having the structural formula

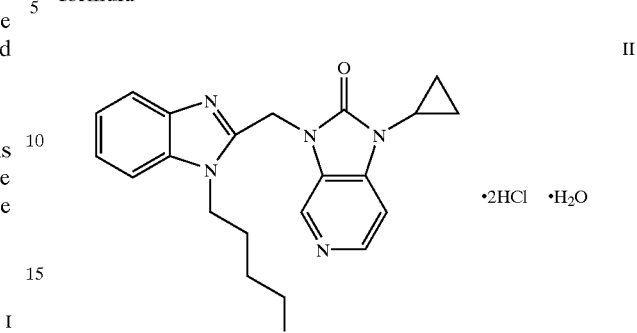

II

DETAILED DESCRIPTION OF THE INVENTION

For the development of pharmaceutical dosage forms, the active ingredient must have acceptable bulk characteristics such as bulk density, compressibility, and flow properties. The anhydrous form P1 of the free base form of the imidazopyridine I displayed undesired bulk characteristics such as a very low bulk density. The bulk material was light, fluffy and difficult to handle. In addition to the anhydrous form P1 two hydrated forms P2 and P3 could be generated in a non-reproducible way. The bulk properties of P2 and P3 were not much improved compared to P1. Therefore, acid addition salts were explored by the present inventors. Based on the pKa values of the two basic functional groups of the imidazopyridine I (5.7 and 3.4) a number of mono and bis protonated addition salts of commonly used acids such as mono and bis methane sulfonate, mono maleate, and mono phosphate were evaluated, in addition to the mono and bis hydrochloride salts.

Crystallinity and satisfactory physical stability of the crystalline form in the solid state is a desirable property of pharmaceutical salt forms. The term physical stability indicates the ability of the salt form to retain its crystal structure including solvents of crystallization, if any, under storage/stress conditions. Significant changes in the physical nature of the salt form as indicated by X-ray analysis or thermal methods such as differential scanning calorimetry are undesirable.

Figure 1:
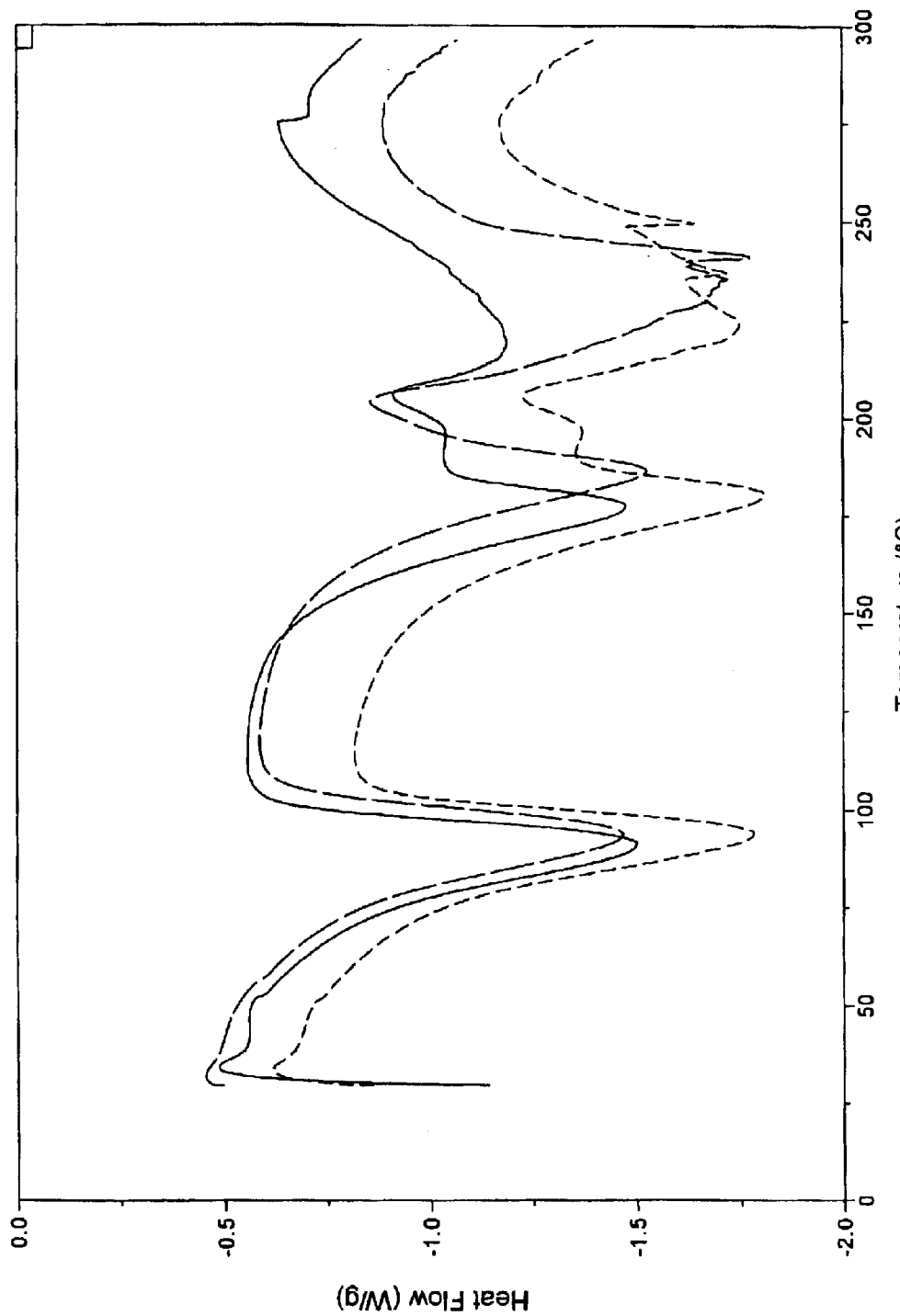
FIG. 1 represents differential scanning calorimetry (TA Instruments DSC 2920) showing physical stability of the bis hydrochloride monohydrate salt. The solid line represents the initial state, short dash represents 6 weeks 40° C./75% RH, long dash represents 6 weeks 50° C. After dehydration at ~100° C., melting/decomposition starts at ~180° C. No major differences can be detected between initial and stressed samples.
Figure 2:
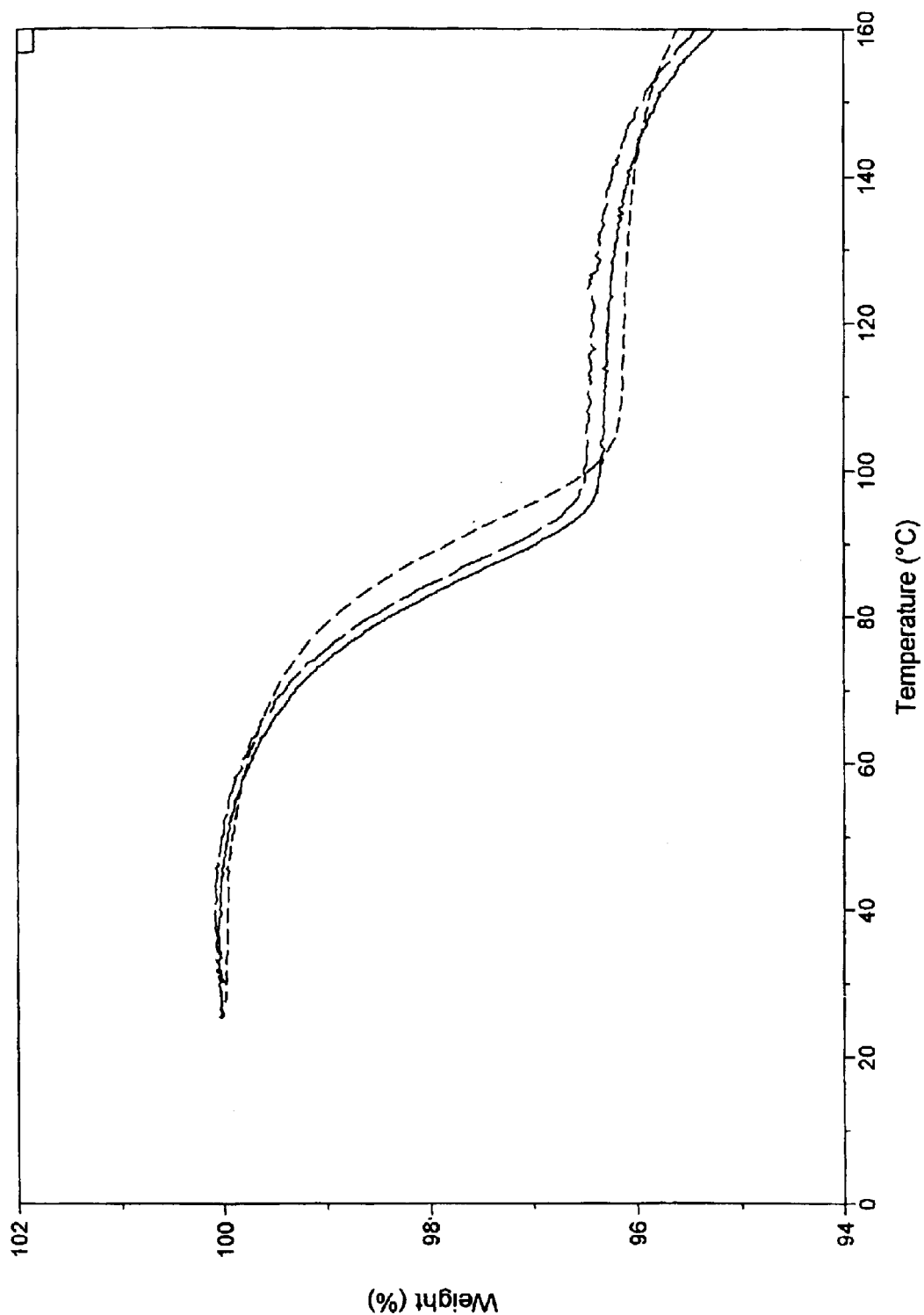
FIG. 2 represents thermogravimetric analysis (TA Instruments TGA 2050) showing physical stability of the bis hydrochloride monohydrate salt. The solid line represents the initial state, short dash represents 6 weeks 40° C./75% RH, long dash represents 6 weeks 50° C. A weight loss of ~3.8% at ~100° C. in all samples indicates the stability of the monohydrate form.
Figure 3:
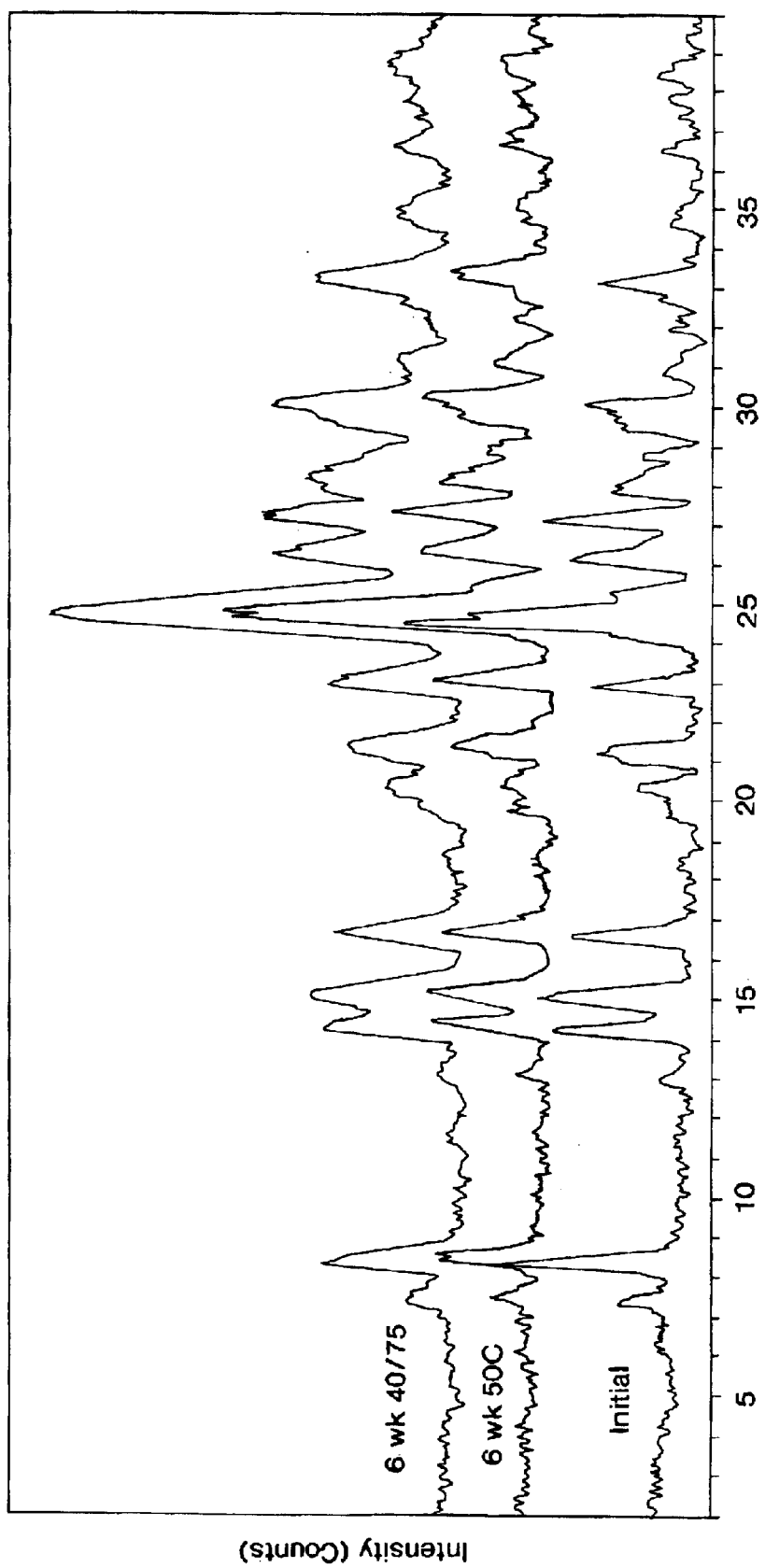
FIG. 3 represent powder X-ray diffraction analysis (Rigaku Miniflex Powder X-ray Diffractometer) showing physical stability of the bis hydrochloride monohydrate salt. The patterns of initial and stressed samples are identical, indicating that no changes in the crystal structure have taken place.

The crystalline bis hydrochloride monohydrate salt of the present invention surprisingly exhibited good bulk characteristics as well as excellent solid state physical stability when stored at 50° C. or 40° C./75% relative humidity (RH) for as long as 6 weeks as shown in FIGS. 1, 2 and 3. Differential scanning calorimetry revealed no significant changes in the thermal behavior of the stressed samples of the bis hydrochloride monohydrate salt compared to that of the unstressed sample (stored at 2–8° C. in closed container). Thermogravimetric analysis as well as Karl Fischer analysis indicated that the crystal structure of the bis hydrochloride monohydrate salt retained its crystal water under above mentioned storage/stress conditions and elemental analysis of the stressed samples revealed that the salt stoichiometry of the bis hydrochloride monohydrate salt remained unchanged. No solid state transformations were observed when the bis hydrochloride monohydrate salt was suspended in water.

Figure 4:
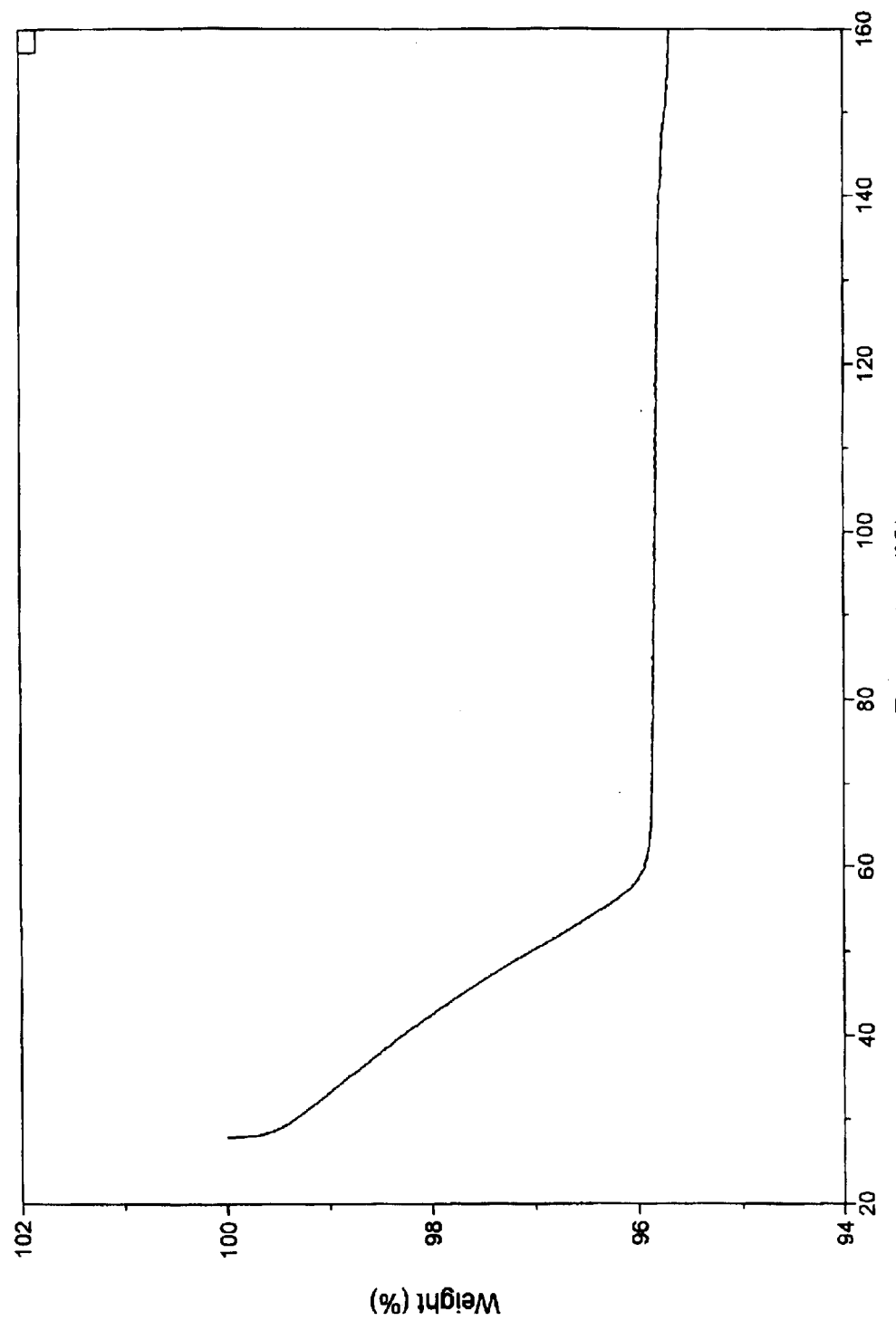
FIG. 4 represents thermogravimetric analysis (TA Instruments TGA 2050) showing the lack of physical stability of the mono phosphate monohydrate salt. Complete dehydration occurs at temperatures below 65° C.
Figure 5:
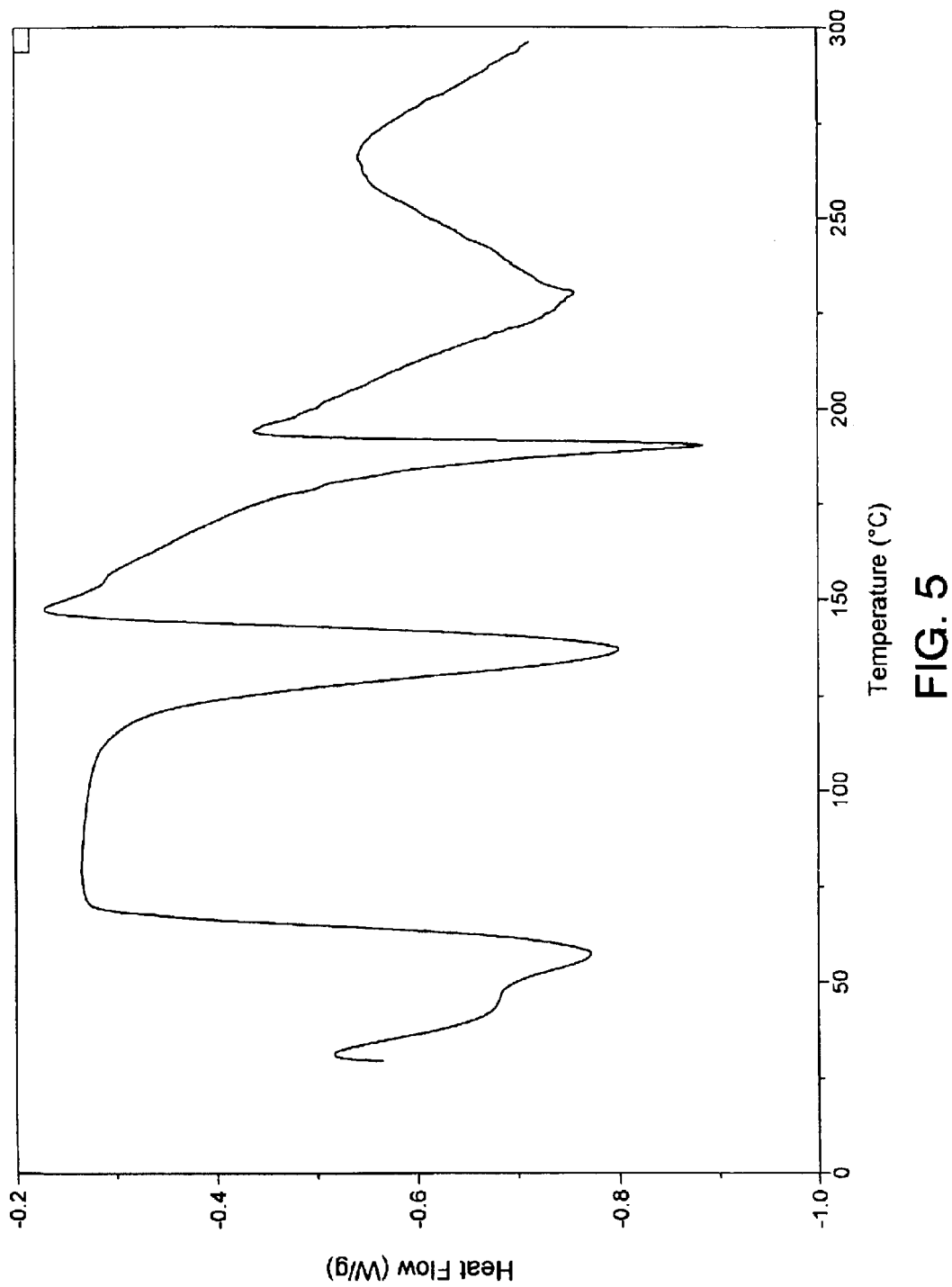
FIG. 5 represents differential scanning calorimetry (TA Instruments DSC 2920) showing the lack of physical stability of the mono phosphate monohydrate salt. Multiple endo- and exothermic solid phase transitions below the melting point indicate the physical instability of the salt.

The mono maleate salt, and the mono phosphate monohydrate salt, on the other hand, showed significant physical instability in the solid state. The mono maleate salt, when suspended in water converted to the fumarate salt as detected by proton NMR analysis. Since fumaric acid (first pKa ~3) is a weaker acid than maleic acid (first pKa ~2) this isomerization of the acid may result in the dissociation to the free base in the solid state. The mono phosphate monohydrate salt lacked the ability to retain the crystal water under storage/stress conditions (FIG. 4). Complete dehydration occurred at temperatures below 65° C. and the obtained dehydrated form converted back to the monohydrate form when cooled back to room temperature. As an additional indication of physical instability in the solid state, the mono phosphate monohydrate salt displayed multiple solid phase transitions below its melting point, as detected by differential scanning calorimetry and variable temperature powder X-ray analysis (FIG. 5). Methyl sulfonate salts could only be generated in the amorphous state, which is not a desirable property for pharmaceutical salt forms.

Further, an anhydrous form of the bis hydrochloride salt was shown to convert rapidly to the bis hydrochloride monohydrate salt of the present invention, when stored between 60 and 70% relative humidity at 25° C. The mono hydrochloride salt could not be generated in a reproducible way, since only mixtures of mono and bis hydrochloride salts or pure bis hydrochloride monohydrate were obtained. The propensity of a particular salt to form solvates or crystal modifications and its ability to retain the solvent of crystallization or the physical stability of crystal modifications under storage/stress conditions cannot be predicted apriori.

For the development of pharmaceutical dosage forms, particularly oral dosage forms, the active ingredient must have sufficient oral bioavailability. A comparison of the oral bioavailability of the imidazopyridine I in dogs revealed that compound I administered as the solid bis hydrochloride monohydrate salt of the present invention in capsules, had similar peak concentrations, shorter times to peak concentrations and greater exposure values than compound I administered as the solid free base in capsules. These pharmacokinetic data can be explained by the higher solubility/dissolution rate of the salt compared to the free base form and they support further that the bis hydrochloride monohydrate salt of the present invention has considerable advantages over the free base form of compound I.

The bis hydrochloride monohydrate salt may be prepared by forming a solution of the free base of compound I with hydrochloric acid in solvents such as acetone, isopropanol, or methanol and then isolating the so produced bis hydrochloride monohydrate salt.

Because of its bioavailability as well as good crystallinity and stability, the bis hydrochloride monohydrate salt is very useful in preparing oral dosage forms of compound I. An example is given below that illustrates the preparation of representative oral formulations.

Biological Activity

The antiviral activity of these compounds against respiratory syncytial virus was determined in HEp-2 (ATCC CCL 23) cells that were seeded in 96 well microtiter plates at $1.5 \times 10^4$ cells/100 µL/well in DMEM (Dulbecco's Modified Eagle's Medium) supplemented with penicillin, streptomycin, glutamine, and 10% fetal bovine serum. The cells were incubated overnight at 37° C., the culture medium was removed, and cells were infected (100 µL volume in medium containing 2% fetal bovine serum) with respiratory syncytial virus Long strain at 5000 plaque forming units/mL. The compounds, 100 µL at appropriate dilution, were added to the cells 1 hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 µL/well of acidified isopropanol (per liter: 900 mL isopropanol, 100 mL Triton X100, and 4 mL conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells with uninfected cells containing compound in the absence of compound provide a measure of cellular toxicity. The control compound in this assay is Ribavirin which exhibits 100% cell protection at 2.5 µg/mL (corresponding to 10.2 µM).

The antiviral activity of compounds, designated as $EC_{50}$, is presented as a concentration that produces 50% cell protection in the assay. The bis-HCl monohydrate salt, compound II, disclosed in this application shows antiviral activity with $EC_{50}$ of 0.06 µM. Ribavirin has an $EC_{50}$ of 3 µM in this assay.

DESCRIPTION OF SPECIFIC EMBODIMENTS

EXAMPLE 1

Preparation of Bis Hydrochloride Monohydrate Salt Compound II from Isopropanol/Water/Acetone Free base compound I (100.0 g, 0.265 mol) was charged into a three-neck round bottom flask with mechanic stirrer and condenser. Isopropanol (400.6 ml) and water (75.0 ml) were added to give a think slurry. Concentrated HCl solution (37% aq., 47.8 ml, 2.2 eq) was added to the mixture. The mixture was heated to 60° C. to form a clear solution. Then acetone (550 ml) was slowly added, while the temperature was maintained at 60° C. The mixture was stirred at 60° C. for one hour before it was slowly cooled to 20–25° C. The mixture was stirred at 20–25° C. for another 2 hours. The solid was filtered, washed with acetone (2×302.5 ml), and dried under vacuum overnight to give 119.3 g (96%) of the bis-HCl monohydrate salt compound II.

Anal. Calcd. $C_{21}H_{23}N_5O_2 \cdot 2.0\ HCl \cdot 1.0H_2O$: C, 53.85; H, 5.81; N, 14.95; Cl, 15.13; $H_2O$, 3.8. Found: C, 53.73; H, 5.75; N, 14.96; Cl, 14.80; $H_2O$, 3.8 (KF).

EXAMPLE 2

Preparation of Capsule Formulations of the Bis Hydrochloride Monohydrate Salt

Capsules (10 and 50 mg free base equivalent) are provided for oral administration in which the capsule size is #0, gray, opaque, hard gelatin capsule containing the bis hydrochloride monohydrate salt of formula II formulated as dry granulation with microcrystalline cellulose, pregelatinized starch, sodium starch glyconate, and magnesium stearate.

We claim:

1. The bis hydrochloride monohydrate salt having the formula

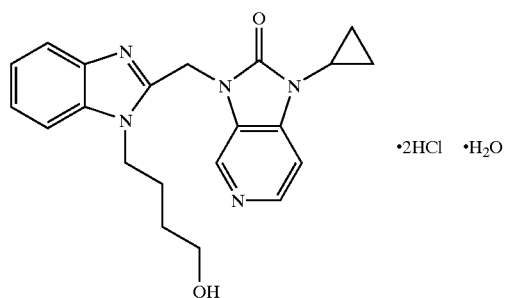

II

·2HCl ·H$_2$O

2. A pharmaceutical dosage form comprising the bis hydrochloride monohydrate salt of claim 1 and a pharmaceutically acceptable carrier.

* * * * *